United States Patent [19]

Hazen et al.

[11] Patent Number: 4,466,914
[45] Date of Patent: Aug. 21, 1984

[54] PROCESS FOR THE CONVERSION OF PRIMARY AND SECONDARY ALCOHOLS TO THEIR CORRESPONDING THIOLS AND THIOL ESTERS

[75] Inventors: George G. Hazen, Westfield; Ralph P. Volante, East Windsor, both of N.J.

[73] Assignee: Merck & Co., Inc., Rahway, N.J.

[21] Appl. No.: 270,321

[22] Filed: Jun. 4, 1981

[51] Int. Cl.$^3$ .................. C07C 149/18; C07C 153/01; C07C 153/017; C07C 153/023
[52] U.S. Cl. ............................. 260/239 A; 260/455 R; 568/62; 568/67; 260/245.2 T; 260/245.2 R
[58] Field of Search .................... 260/455 R, 245.2 T, 260/239 AL, 245.2 R; 568/62, 67

[56] References Cited

PUBLICATIONS

Hojo et al., Chem. Lett., 437, 1977.
Hojo et al., Chem. Lett., 133, 1977.
King, et al., Tetrahedron Lett., 3615, 1979.
Damico, et al., Phosphor Sulfur Related Elem., 7 (3), 301, 1979.
Mitsunobu et al., Bull. Chem. Soc. Jap., 44, 3427, 1971.
Mitsunobu et al., Bull. Chem. Soc. Jap., 40, 2380, 1967.
Mitsunobu, Synthesis 1, 1981.
Mukaiyawa, et al., Tetrahedron Lett., 1901, 1970.
Mukaiyawa, et al., Ang. Chem. Int. Ed. Eng., 15, 94, 1976.
Beretta, et al., Synthesis, 425, 1974.
Mitsunobu, et al., J. Amer. Chem. Soc., 94, 679, 1972.

*Primary Examiner*—Henry R. Jiles
*Assistant Examiner*—Robert C. Whittenbaugh
*Attorney, Agent, or Firm*—Daniel T. Szura; Hesna J. Pfeiffer

[57] ABSTRACT

Disclosed is a mild, efficient, stereo-selective process for a one step conversion of primary and secondary alcohols to their corresponding thiol ester and thiol derivatives with inversion of configuration. The process comprises the reaction of the alcohol in question (4), the thiolacid of choice (5) in the presence of adduct 3; the resulting thiol ester 6 may be converted to the free thiol 7 by hydrolysis or reductive methods:

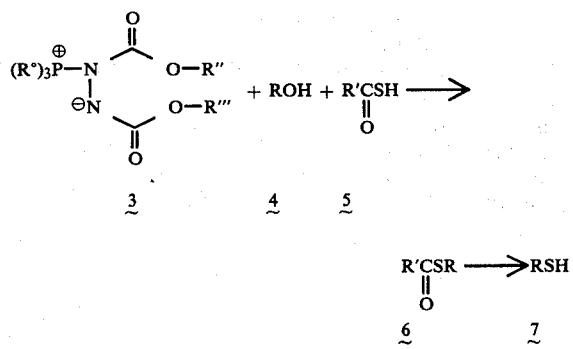

5 Claims, No Drawings

PROCESS FOR THE CONVERSION OF PRIMARY AND SECONDARY ALCOHOLS TO THEIR CORRESPONDING THIOLS AND THIOL ESTERS

BACKGROUND OF THE INVENTION

This invention relates to a mild, efficient, stereoselective method for the one step conversion of primary and secondary alcohols to their corresponding thiol ester and thiol derivatives with inversion of configuration:

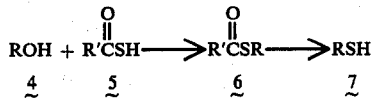

wherein ROH is the alcohol taken in reaction and wherein R'COSH is the thiolacid reagent of choice. The transformation of the resulting thiol ester 6 to the corresponding thiol 7 is achieved by saponification or by reductive methods. The process of the present invention permits the above transformation upon alcohols which heretofore would have been considered too labile to undergo conventional transformation to the corresponding thiol analogue. Alcoholic substrates 4 of primary interest are indicated below as are their corresponding thiol ester and thiols.

All prior methods for the conversion of an alcohol to a thiol ester or thiol consist of a series of chemical reactions. The alcohols are first converted to an activated species (halide or tosylate, for example) and then displaced with a suitable sulfur containing nucleophile. These transformations are often not applicable to sensitive molecules, such as beta-lactams, due to the harshness of reaction conditions typically employed and the accompanying by-products produced.

The process of the present invention, however, differs from known methodology as the alcoholic substrates are converted directly to the thiol ester derivatives in one step under very mild reaction conditions. Thus alcohols containing other sensitive functionality (such as the beta-lactan) can be successfully transformed to their corresponding thiol derivatives in high yield. The process of the present invention is also more efficient and of higher stereoselectivity than prior methods. The recited advantages of the process of the present invention are in part attributable to the use of the triphenylphosphine-diisopropyl azodicarboxylate mediated hydroxyl activation with subsequent thiol acid displacement.

A class of alcoholic substrates which are converted to their corresponding thiol ester and thiol forms by the process of the present invention include thienamycin intermediates, described below, which are useful, for example, in preparing the known thiol and thiol ester analogues of thienamycin:

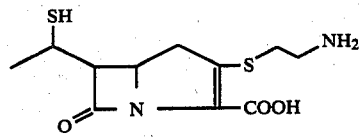

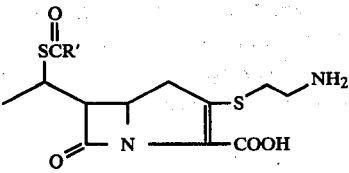

wherein R' is loweralkyl having 1-6 carbon atoms.

Still in the area of nonclassical beta-lactam carbapenem antibiotics such as thienamycin, it should be noted that the transformation made available by the process of the present invention is preferably applied to intermediates in the synthesis of such final carbapenem products. Thus, for example, in the preparation of thienamycin the intermediate azetidinones which bear the hydroxyethyl substituent may be converted to the thiol or thiol ester for subsequent elaboration to desired species such as those shown above. The following azetidinones are representative of such alcoholic substrates that may be employed in this process. Such azetidinones are disclosed in the following publications which are incorporated herein by reference D. G. Melillo, I. Shinkai, T. Liu, K. Ryan, M. Sletzinger, *Tet. Lett.* 2783, 1980; T. N. Salzmann, R. W. Ratcliffe, F. A. Bouffard, and B. G. Christensen, *J. Am. Chem. Soc.* 102, 6161, 1980.:

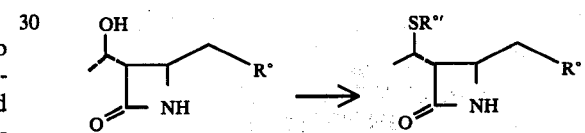

wherein R°' is hydrogen and as previously defined; R°' is:

$CO_2CH_3$
$CO_2C_6H_5$
$CO_2PNB$
(PNB = p-nitrobenzyl)

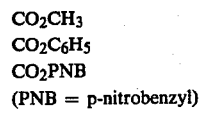
(Alkyl has 1-6 carbon atoms)

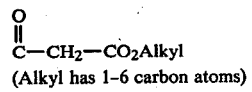
(Aryl, such as, phenyl and substituted phenyl)

Other alcohols ROH which may be transformed to their corresponding thiol and thiol esters are demonstrated in the following table:

| Compound | ROH | RSH |
|---|---|---|
| 1. | 2(−)octanol | 2(+)octane thiol |
| 2. | 3-β-cholesterol | 3α-cholesteryl thiol |
| 3. | benzyl alcohol | benzyl-mercaptan |
| 4. | cinamyl alcohol | cinamyl thiol |

The process of the present invention can also be used for the synthesis of various mercapto analogues of prostaglandins and thromboxanes, for example, 15 epi PGA₂ methylester can be converted to the 15-thioacetyl PGA₂ methyl ester. Selective hydrolysis to the 15 mercapto—PGA₂ methyl ester of similar utility is accomplished by hydrolysis with methanolic HCl or sodium methoxide in methanol.

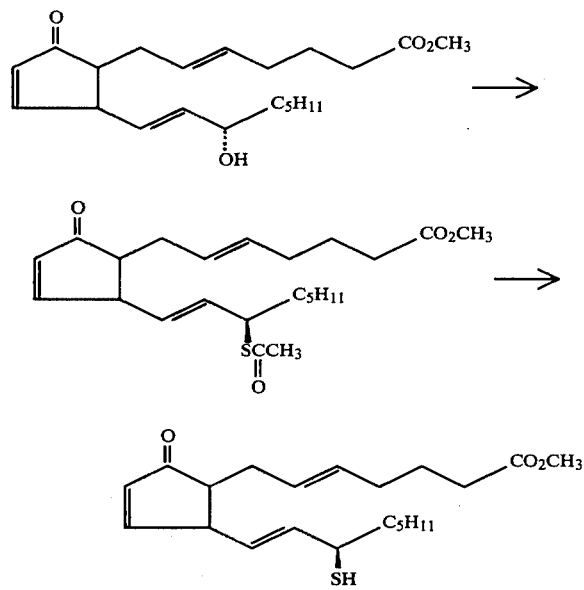

DETAILED DESCRIPTION OF THE INVENTION

The process of the present invention may be conveniently demonstrated by the following scheme:

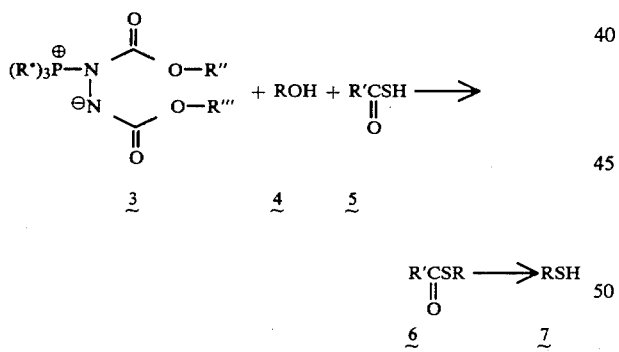

In words relative to the above diagram, the alcohol of choice 4 in the presence of the triphenylphosphine-diisopropyl azodicarboxylate hydroxyl activating reagent 3 is subjected to thiol acid displacement with reagent 5 wherein R' is loweralkyl having 1-6 carbon atoms, phenyl, substituted phenyl, or the like. The resulting thiol ester 6 can be converted to the free thiol by either saponification or reductive methods. The preformation of adduct 3 is essential in this sequence as it prevents deactivation of the dicarboxylate by reaction with the thiol acid 5. The following reaction is illustrative for the preparation of a preferred activating agent 3:

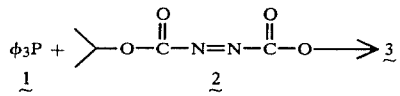

the initial preparation of adduct 3 by treatment of triphenylphosphene 1 with diisopropyl dicarboxylate 2 is accomplished in a solvent such as tetrahydrofuran-methylene chloride, diethylether, toluene or the like at a temperature of from −10° to 10° C. for from 0.5-2 hours. The preformed adduct 3 is then treated with the alcohol of choice 4 and the thiol acid 5 in a solvent such as tetrahydrofuran, methylene chloride diethylether, toluene, or the like. The resulting mixture is stirred for from 1-2 hours at a temperature of from 0° to 10° C. whereupon the temperature is raised to a range of from 25°-45° C. and stirring is continued for from 1-2 hours.

The resulting thiol ester 6 may be isolated by conventional procedures such as distillation or chromatography. The thiol esters 6 can then be converted to the free thiol by either saponification or reductive measures. Typically, 6 is converted to 7 on treatment with lithium aluminum hydride in ether or in aqueous sodium hydroxide solution. In the alternative, 6 may be converted to 7 by catalytic hydrogenation. A preferred value for R' under such hydrogenation scheme is 1,1-dimethyl o-nitrophenoxymethinyl:

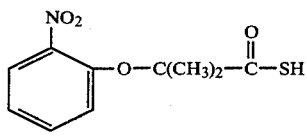

The above illustrated hydroxyl activated agent 3 may generically be represented by the following generalized structure:

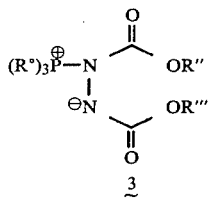

wherein R° is selected from the group consisting of phenoxy, phenyl, alkoxyl (having 1-6 carbon atoms), alkyl (having 1-6 carbon atoms) or the like; and R″ and R‴ independently selected from the group consisting of alkyl (having 1-6 carbon atoms), or phenyl or the like.

As stated above, the process of the present invention provides a stereoselective method with inversion. The inversion occurs by conversion of the alcohol 4 to the intermediate alkoxy-phosphonium salt with retention of configuration. The intermediate alkoxy-phosphonium salt then undergoes displacement by thiolacid anion 5 in a highly stereoselective and regioselective manner to produce the inverted thiolesters 6.

EXAMPLE 1

Preparation of benzyl
[2R-[2β,3α,(Rγ)]]-3-(1-thioacetylethyl-4-oxo-2-azetidine acetate 8;
[2R-[2β,3α,(Sγ)]]-3-(1-hydroxyethyl)-oxo-2-azetidine acetate 7

Diisopropyl azodicarboxylate (0.62 g, 3.0 mmol) is added to a solution of triphenylphosphine (0.79 g, 3.0 mmol) in 10 ml of tetrahydrofuran at 0°. The mixture is stirred at 0° for 30 minutes. A white precipitate results. A mixture of benzyl [2R,-[2β, 3α, (Rγ)]]-3-(1-hydroxyethyl)-4-oxo-2-azetidine acetate (0.53 g, 2.0 mmol) and thiolacetic acid (0.38 g, 5.0 mmol) in 2 ml tetrahydrofuran is added dropwise and the mixture is stirred for 1 hour at 0° and 1 hour at 22°–25°. The mixture is concentrated in vacuo and purified by preparative layer chromatography on silica gel (elution with 6:4 hexane-ethyl acetate) to yield 0.3 g of desired thiol acetate (54%).

Preparation of benzyl [2R-[2β, 3α, (Rγ)]]-3-(1-mercaptoethyl)-4-oxo-2-azetidineacetate Thioacetylazedidinone 7 (1.69 g, 5 mmol) is dissolved in 25 ml of MeOH and treated with 25 ml of 1 M aqueous sodium hydroxide solution. The mixture is stirred 1–2 hours at 22°–25°. The mixture is diluted with 50 ml water and extracted with 2–50 ml portions of diethylether. The combined ethereal portions are dried over sodium sulfate and concentrated in vacuo to give 1.32 g of mercaptobenzylester as a clear oil (95% yield).

EXAMPLE 2

Preparation of S(+)-2-Octanethiol

Diisopropyl azodicarboxylate (8.33 g, 40 mmol) is added to an efficiently stirred solution of triphenylphosphine (10.50 g, 40 mmol) in 100 ml of tetrahydrofuran at 0°. The mixture is stirred at 0° for 30 minutes. A white precipitate results. R(−)-2-octanol (2.6 g, 20 mmol, $[\alpha]_D^{25}$ neat= −8.0°, theory −9.9°, 80.8% optical purity) and thiolacetic acid (3.04 g, 40 mmol) in 50 ml of tetrahydrofuran is added dropwise over 10 minutes. The mixture is stirred at 0° for 1 hour and at 22°–25° for 1 hour. A clear yellow solution results. The solution is concentrated and then purified by column chromatography over silica gel (elution with hexane-methylene chloride, 1:1) to give 3.70 g (98%) of the desired S(+)-2-octanethiol acetate.

Thiol acetate (3.0 g, 15.95 mmol) is dissolved in 25 ml of anhydrous ether and added dropwise to a suspension of lithium aluminum hydride (0161 g, 4.0 equiv) in 15 ml of anhydrous ether under a nitrogen atmosphere. The reaction mixture is stirred at 22°–25° for 30 minutes and the excess lithium aluminum hydride is destroyed by the careful addition of 10 ml of 1 N hydrochloric acid solution. The ether layer is separated and dried over sodium sulfate to give 2.37 g(100%) of S(+)-2-octane thiol as a clear oil. This material is homogeneous by nmr. An analytical sample was prepared by distillation (2.05 g, 88.6%, 65°–70°, 15 torr, Lit. Bp. 80°–22°, 25 torr).

EXAMPLE 3

Preparation of:

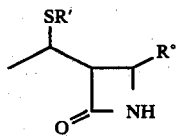

Follow the procedure of the foregoing Examples and text, the following compounds are prepared when the indicated substitution is made.

| compound | R' | R° |
| --- | --- | --- |
| 1. | O<br>‖<br>C—CH$_3$ | —CO$_2$Bz |
| 2. | O<br>‖<br>C—CH$_3$ | O<br>‖<br>—CH$_2$—C—CH$_2$—CO$_2$PNB |
| 3. | O<br>‖<br>—C—CH$_3$ | —CH$_2$—CO$_2$Me |

EXAMPLE 4

Following the text and foregoing examples the following thiols are obtained from the starting alcohol.

TABLE 1

| Compound | ROH | RSH |
| --- | --- | --- |
| 1. | 2-octanol | 2-thioloctanol |
| 2. | cinnanyl alcohol | cinnamyl thiol |
| 3. | β-cholesterol | α-mercapto cholesterol |
| 4. | epi PGA$_2$ methylester | 15-mercapto PGA$_2$ methylester |

What is claimed is:

1. A process for preparing mercaptans RSH comprising the step of treating the alcohol ROH with thiol acid R' COSH in the presence of hydroxyl activating reagent selected from the group consisting of triphenyl phosphine-dialkylazodicarboxylate or triphenylphosphite-dialkylazodicarboxylate followed by hydrolytic or reductive cleavage of the radical R' CO to yield the mercaptan RSH; wherein R' is selected from the group consisting of lower alkyl having 1–6 carbons, phenyl or phenyl substituted by chloro, nitro, or methoxyl; wherein the alcohol ROH is a primary or secondary alkanol having 1–12 carbon atoms and wherein the molar ratio of alcohol to thiol acid to hydroxyl activating reagent is 1:1:1 or more.

2. A process for preparing the thiol ester R$^1$COSR comprising the steps of treating the alcohol ROH with thiol acid R$^1$COSH in the presence of an hydroxyl activating reagent selected from the group consisting of triphenylphosphine-dialkyl-azodicarboxylate, or triphenylphosphite-dialkyl-azodicarboxylate wherein R$^1$ is selected from the group consisting of lower alkyl having 1–6 carbons, phenyl, or phenyl substituted by chloro, nitro, or methoxy; wherein the alcohol ROH is a primary or secondary alkanol having 1–12 carbon atoms and wherein the molar ratio of alcohol to thiol acid to hydroxyl activating reagent is 1:1:1 or more.

3. A process according to claim 1 or 2 wherein the alcohol ROH is selected from the group consisting of:

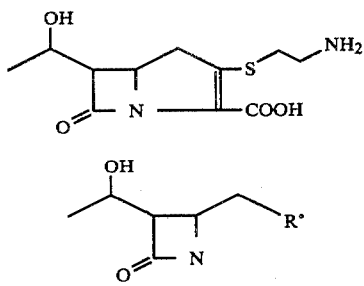

R° is selected from: $CO_2CH_3$, $CO_2C_6H_5$, $CO_2PNB$, PNB=p-nitrobenzyl,

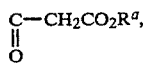

$R^a = C_{1-6}$ alkyl, or phenyl.

4. A process for preparing mercaptans RSH comprising the steps of treating the alcohol ROH with thiol acid R′ COSH in the presence of a hydroxyl activating reagent selected from the group consisting of triphenyl phosphine-dialkylazodicarboxylate or triphenylphosphite- dialkylazodicarboxylate followed by hydrolytic or reductive cleavage of the radical R′ CO to yield the mercaptan RSH; wherein R′ is selected from the group consisting of lower alkyl having 1-6 carbons, phenyl or phenyl substituted by chloro, nitro, or methoxyl; wherein the alcohol ROH is selected from:

2(—)octanol,
3-β-cholesterol,
benzyl alcohol,
cinamyl alcohol,
15-epi-PGA$_a$methylester, wherein the molar ratio of alcohol to thiol acid to hydroxyl activating reagent is 1:1:1 or more.

5. A process for preparing the thiol ester R′COSR comprising the steps of treating the alcohol ROH with thiol acid R′COSH in the presence of an hydroxyl activating reagent selected from the group consisting of triphenyl phosphine-dialkyl- azodicarboxylate or triphenylphosphite-dialkyl- azodicarboxylate wherein R′ is selected from the group consisting of lower alkyl having 1-6 carbons, phenyl, or phenyl substituted by chloro, nitro, or methoxyl; wherein the alcohol ROH is selected from:

2(—) octanol,
3-β-cholesterol,
benzyl alcohol,
cinamyl alcohol,
15-epi-PGA$_2$ methyl ester and wherein the molar ratio of alcohol to thiol acid to hydroxyl activating reagent is 1:1:1 or more.

* * * * *